(12) United States Patent
Wigbers et al.

(10) Patent No.: US 8,772,547 B2
(45) Date of Patent: Jul. 8, 2014

(54) METHOD FOR PRODUCING 1-ADAMANTYL TRIMETHYLAMMONIUM HYDROXIDE

(75) Inventors: Christof Wilhelm Wigbers, Mannheim (DE); Martin Ernst, Heidelberg (DE); Laszlo Szarvas, Ludwigshafen (DE); Giovanni D'Andola, Heidelberg (DE); Ellen Dahlhoff, Limburgerhof (DE); Gabriele Iffland, Heidelberg (DE); Peter Raatz, Ludwigshafen (DE); Falk Simon, Bensheim (DE); Matthias Frauenkron, Freinsheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/255,805

(22) PCT Filed: Mar. 11, 2010

(86) PCT No.: PCT/EP2010/053077
§ 371 (c)(1),
(2), (4) Date: Sep. 9, 2011

(87) PCT Pub. No.: WO2010/103062
PCT Pub. Date: Sep. 16, 2010

(65) Prior Publication Data
US 2012/0010431 A1    Jan. 12, 2012

(30) Foreign Application Priority Data
Mar. 12, 2009 (EP) .................... 09155016

(51) Int. Cl.
*C07C 211/00* (2006.01)

(52) U.S. Cl.
USPC ........................................ 564/459

(58) Field of Classification Search
None
See application file for complete search history.

(56) References Cited

U.S. PATENT DOCUMENTS

| | | | |
|---|---|---|---|
| 3,310,469 A | 3/1967 | Paulshock et al. | |
| 4,613,705 A * | 9/1986 | Hargis | 564/409 |
| 6,248,798 B1 * | 6/2001 | Slingsby et al. | 521/28 |
| 6,455,528 B1 * | 9/2002 | Adachi et al. | 514/252.14 |
| 2007/0142642 A1 | 6/2007 | Szarvas et al. | |
| 2007/0254822 A1 | 11/2007 | Szarvas et al. | |
| 2010/0191000 A1 | 7/2010 | Melder et al. | |
| 2010/0240894 A1 | 9/2010 | Ernst et al. | |
| 2010/0261015 A1 | 10/2010 | Szafranski et al. | |
| 2010/0267596 A1 | 10/2010 | Degen et al. | |
| 2010/0270140 A1 | 10/2010 | Siegert et al. | |
| 2010/0310853 A1 | 12/2010 | Schwiegk et al. | |
| 2010/0311973 A1 | 12/2010 | Ernst et al. | |
| 2011/0021789 A1 | 1/2011 | Windecker et al. | |
| 2011/0033361 A1 | 2/2011 | Chedid et al. | |
| 2011/0060166 A1 | 3/2011 | Ernst et al. | |
| 2011/0124918 A1 | 5/2011 | Ernst et al. | |
| 2011/0124919 A1 | 5/2011 | Ernst et al. | |
| 2011/0172430 A1 | 7/2011 | Ernst et al. | |

FOREIGN PATENT DOCUMENTS

| | | |
|---|---|---|
| BE | 646581 | 7/1964 |
| EP | 0 139 504 | 5/1985 |
| EP | 0 231 018 | 8/1987 |
| WO | 2005 085207 | 9/2005 |
| WO | 2005 115969 | 12/2005 |

OTHER PUBLICATIONS

Vashkevich, E. V. et al., "Synthesis of Surfactants Derived From Adamantane", Russian Journal of Applied Chemistry, vol. 74, No. 11, pp. 1892-1898, XP-002578328, (2001).
International Search Report Issued May 25, 2010 in PCT/EP10/053077 filed Mar. 11, 2010.
U.S. Appl. No. 13/127,828, filed Aug. 5, 2011, Wigbers, et al.
U.S. Appl. No. 13/128,508, filed May 10, 2011, Dahmen, et al.

* cited by examiner

*Primary Examiner* — Clinton Brooks
(74) *Attorney, Agent, or Firm* — Oblon, Spivak, McClelland, Maier & Neustadt, L.L.P.

(57) ABSTRACT

The present invention relates to a process for preparing 1-adamantyltrimethylammonium hydroxide, by A) reacting 1-adamantyldimethylamine with dimethyl sulfate to give 1-adamantyltrimethylammonium sulfate; and B) subjecting the 1-adamantyltrimethylammonium sulfate obtained in A) to anion exchange with an ion exchanger loaded with OH ions.

20 Claims, No Drawings

METHOD FOR PRODUCING 1-ADAMANTYL TRIMETHYLAMMONIUM HYDROXIDE

The present invention relates to a process for preparing 1-adamantyltrimethylammonium hydroxide.

1-Adamantyltrimethylammonium hydroxide is of interest, for example, for the preparation of catalysts—for example, as a template in the synthesis of zeolites, which in turn can be used as a catalyst (component). There is therefore a need for economic routes to its preparation.

For the preparation of ammonium salts of organic amines it is long-established practice to alkylate amines with dialkyl sulfates, although generally utilizing only one alkyl group of the dialkyl sulfate, hence resulting in the corresponding monoalkyl sulfate salts.

WO 2005/085207 describes a process for preparing ionic compounds comprising cations having quaternary $sp^2$-hybridized nitrogen atoms, by reacting compounds comprising a doubly bonded nitrogen atom with a dialkyl sulfate at elevated temperature and using both alkyl groups of the dialkyl sulfate, to give an ionic compound having sulfate anions, and subjecting said compound optionally to anion exchange. The anion exchange may take place by transprotonation, reaction with a metal salt, ion exchange chromatography, electrolysis or a combination of these measures.

WO 2005/115969 relates to a process for preparing quaternary ammonium compounds by reacting an amine compound comprising at least one $sp^3$-hybridized nitrogen atom with a dialkyl sulfate, using both alkyl groups of the dialkyl sulfate, to give a quaternary ammonium compound having sulfate anions, and subsequently exchanging the sulfate anion for a different anion. The anion exchange may take place as described in WO 2005/085207.

BE 646581 describes derivatives of adamantane, various processes for their preparation, and their medical use, as antivirals, for example. Thus, for example, the alkylation of 1-aminoadamantane with methyl iodide to give 1-adamantyltrimethylammonium iodide, the further reaction with aminoethanol to give 1-adamantyldimethylamine, and its isolation as a salt of perchloric acid are described. Disadvantages associated with the use of methyl iodide for the alkylation are that product mixtures with different degrees of alkylation are always obtained, and the high price of said iodide.

EP 0 139 504 A1 describes a process for catalytic paraffin-olefin alkylation, using a catalyst which comprises at least one adamantane derivative. The adamantane derivatives said to be suitable include 1-adamantyltrimethylammonium salts, with sulfate mentioned as a preferred anion.

EP 0 231 018 A2 describes a crystalline zeolite and its preparation using quaternary ammonium compounds of adamantane. Example 1 of said document describes the preparation of 1-adamantyltrimethylammonium hydroxide by alkylation of 1-aminoadamantane with methyl iodide and subsequent exchange of the iodide anions on an ion exchanger loaded with OH ions.

Surprisingly it has been found that 1-adamantyltrimethylammonium hydroxide can be prepared advantageously by starting from 1-adamantyldimethylamine, subjecting it to alkylation with dimethyl sulfate, and then subjecting the alkylation product to anion exchange on an ion exchanger loaded with OH ions. Success is achieved here in producing, in the alkylation with dimethyl sulfate, essentially the 1-adamantyltrimethylammonium salt of the sulfate ($SO_4^{2-}$) and not of the methylsulfate (methosulfate, $CH_3OSO_3^-$). The 1-adamantyltrimethylammonium salt of the sulfate is notable for its high affinity for ion exchanger resins and can be subjected more effectively to anion exchange than the 1-adamantyltrimethylammonium salt of the methylsulfate.

The invention accordingly provides a process for preparing 1-adamantyltrimethylammonium hydroxide, by
A) providing 1-adamantyldimethylamine and subjecting it to a reaction with dimethyl sulfate in which essentially both methyl groups of the dimethyl sulfate are consumed by reaction, to give, essentially, 1-adamantyltrimethylammonium sulfate, and
B) subjecting the 1-adamantyltrimethylammonium sulfate obtained in step A) to anion exchange on an ion exchanger loaded with OH ions.

Step A)

The 1-adamantyldimethylamine may be provided in step A) by subjecting 1-adamantylamine or a 1-adamantylammonium salt to an alkylation in the sense of a dimethylation. Substantially, both methyl groups of the dimethyl sulfate react. By "substantially both methyl groups of the dimethyl sulfate react" is meant in the context of the present invention that at least 90%, preferably at least 95% of the two methyl groups of the dimethyl sulfate react. Accordingly, the methylation product obtained in the reaction contains at most 10%, preferably at most 5%, more particularly at most 1% by weight of methosulfate, $CH_3OSO_3^-$. In one specific embodiment the methosulfate content is well below 1%, especially below 0.5%, or below 0.1% by weight.

The 1-adamantyldimethylamine is preferably provided starting from 1-adamantylammonium hydrochloride.

In one specific embodiment of the process of the invention the 1-adamantylammonium hydrochloride is first converted into 1-adamantylamine. This can be done by reacting the 1-adamantylammonium hydrochloride with aqueous base. Examples of suitable bases include alkali metal hydroxides, such as NaOH or KOH.

The reaction of the 1-adamantylammonium hydrochloride with aqueous base takes place preferably in the presence of an organic solvent which is water-immiscible and in which the 1-adamantylamine formed dissolves. A water-immiscible organic solvent in the context of the present invention is a solvent which under standard conditions (20° C., 1013 mbar) dissolves to an extent of not more than 10 g in 100 g of water, and in which under standard conditions not more than 10 g of water dissolve in 100 g of solvent. Suitable organic solvents are aromatic hydrocarbons, such as benzene, toluene, ethylbenzene or xylene; halogenated solvents, such as dichloromethane, chloroform, carbon tetrachloride, dichloroethane or chlorobenzene; aliphatic solvents, such as pentane, hexane, heptane, octane, ligroin, petroleum ether, cyclohexane or decalin; and mixtures thereof. Toluene or xylene is preferred. The reaction then takes place as an extractive reaction, the amine liberated undergoing essentially complete transfer to the organic phase. The 1-adamantylamine can be isolated by removing the organic solvent by customary methods, such as evaporation. The evaporation of the solvent may take place in apparatus customary for the purpose. Solvent evaporation takes place preferably under reduced pressure and/or at elevated temperature. For the further reaction it is preferred to use the 1-adamantylamine as a solution in the organic solvent.

In a first version of the process of the invention, the 1-adamantyldimethylamine is provided in step A) by subjecting formaldehyde to reductive amination with 1-adamantylamine or a 1-adamantylammonium salt and with hydrogen in the presence of a hydrogenation catalyst.

Where a 1-adamantylammonium salt is used for the reductive amination in accordance with the first version, the salt in question is preferably 1-adamantylammonium hydrochloride. An alternative to this, for the reductive amination in accordance with the first version, is to use 1-adamantylamine which is obtainable by prior reaction of 1-adamantylammonium hydrochloride with an aqueous base, as described above.

For the reductive amination in accordance with the first version a solvent or solvent mixture is used which is inert under the reaction conditions. Those suitable include water, organic solvents, and mixtures thereof. Also suitable are combinations of solvents which are wholly or partly immiscible with one another. In one preferred embodiment the reaction takes place in a system which has two liquid phases. Suitable organic solvents are preferably selected from alcohols, such as methanol, ethanol, n-propanol, isopropanol, n-butanol, tert-butanol or phenol, diols and polyols, such as ethanediol and propanediol, aromatic hydrocarbons, such as benzene, toluene, ethylbenzene or xylenes, halogenated solvents, such as dichloromethane, chloroform, carbon tetrachloride, dichloroethane or chlorobenzene, aliphatic solvents, such as pentane, hexane, heptane, octane, ligroin, petroleum ether, cyclohexane or decalin, ethers, such as tetrahydrofuran, diethyl ether, methyl tert-butyl ether or diethylene glycol monomethyl ether, and mixtures thereof. For the reductive amination it is preferred to use a mixture of water and at least one water-immiscible organic solvent. Preference is given to a mixture which comprises water and at least one aromatic hydrocarbon, such as benzene, toluene, ethylbenzene or xylene. One specific embodiment uses a water/xylene mixture.

The reaction temperature is preferably in a range from 20 to 250° C., more particularly from 50 to 200° C.

The pressure is preferably in a range from 1 to 300 bar, more preferably from 5 to 200 bar, more particularly from 10 to 150 bar.

The formaldehyde is used preferably in the form of an aqueous solution. The formaldehyde content of the aqueous solution is preferably in a range from about 10% to 40%, preferably about 20% to 35% (depending on conditions, a saturated aqueous formaldehyde solution has a formaldehyde content of 36% to 40%).

For reductive amination according to the first version, using water or water-containing solvent mixtures, a buffer may be added to the aqueous phase in order to adjust the pH. Preferably the buffer is selected such that the pH of the aqueous phase during the reaction is in a range from about 5 to 10 and preferably about 7 to 10. A preferred buffer substance is $NaH_2PO_4$. The addition of $NaH_2PO_4$ may also be advantageous for its capacity to prevent corrosion by forming corrosion-inhibiting outer layers.

The molar amount ratio of formaldehyde to 1-adamantylamine (or the 1-adamantylammonium salt) is preferably in a range from 1.8:1 to 10:1, more preferably from 2.0:1 to 5:1, more particularly 2.01:1 to 3:1.

As hydrogenation catalyst it is possible to use commercially customary catalysts. Of particular suitability are catalysts which comprise palladium, rhodium, ruthenium, platinum, iron, cobalt, copper and/or nickel as hydrogenation-active metals.

The hydrogenation catalyst used preferably comprises a Raney metal, more preferably Raney nickel.

Also suitable as a hydrogenation catalyst, preferably, are catalysts comprising palladium as an active component. Besides palladium, the catalyst may also comprise further active components, preferably selected from zinc, cadmium, platinum, silver, rare earth metals, and mixtures thereof. One suitable rare earth metal is cerium.

Prior to its further reaction with dimethyl sulfate, the reductive amination product obtained in accordance with the first version of the process of the invention can be subjected to a workup. A distillative workup is preferred.

One preferred embodiment is a process wherein
a) 1-adamantylammonium hydrochloride is converted by reaction with an aqueous solution of a base into 1-adamantylamine,
b) the 1-adamantylamine is subjected to reductive amination with formaldehyde and hydrogen in the presence of a hydrogenation catalyst, to give 1-adamantyldimethylamine,
c) the 1-adamantyldimethylamine is subjected to reaction with dimethyl sulfate, essentially both methyl groups of the dimethyl sulfate being consumed by reaction, to give, essentially, 1-adamantyltrimethylammonium sulfate, and
d) the 1-adamantyltrimethylammonium sulfate is subjected to anion exchange on an ion exchanger loaded with OH ions.

With regard to steps a) and b), reference is made in their entirety to the earlier remarks concerning the conversion of 1-adamantylammonium hydrochloride into 1-adamantylamine and the catalytic reductive amination with formaldehyde and hydrogen. With regard to steps c) and d), reference is made in their entirety to the remarks below concerning the reaction of the 1-adamantyldimethylamine with dimethyl sulfate and the anion exchange on an ion exchanger loaded with OH ions (i.e., step B).

In a second version of the process of the invention, the 1-adamantyldimethylamine is provided in step A) by subjecting formaldehyde to reductive amination with 1-adamantylamine or a 1-adamantylammonium salt in the presence of formic acid. The reductive alkylamination of carbonyl compounds in the presence of formic acid is known in the literature under the designation of the Leuckart reaction. The reductive aminomethylation with formaldehyde as a carbonyl component in the presence of formic acid is referred to as the Eschweiler-Clark reaction. Suitable reaction conditions are found in, for example, J. March, Advanced Organic Chemistry, John Wiley & Sons, 4th edition, pp. 898 to 900, and the literature cited therein, hereby incorporated in its entirety by reference.

For the reductive amination in accordance with the second version it is preferred to use 1-adamantylammonium hydrochloride. It is, however, also possible to start from 1-adamantylamine for the reductive amination in accordance with the second version.

For the reductive amination in accordance with the second version it is possible to use a solvent or solvent mixture which is inert under the reaction conditions, as described above very generally and more specifically in the context of the first version. In one specific embodiment, water is used. For the reaction in accordance with the second version it is possible, for example, first to dissolve the 1-adamantylammonium hydrochloride in an aqueous formaldehyde solution. For this purpose the aqueous formaldehyde solution may be heated to a temperature of about 30 to 80° C. Subsequently, the formic acid is then added for the reaction. The reaction temperature following addition of the formic acid is preferably in a range from 20 to 200° C., more particularly from 40 to 150° C.

The formaldehyde content of the aqueous solution is preferably in a range from about 10% to 40%, preferably about 20% to 35%.

The molar amount ratio of formaldehyde to 1-adamantylammonium hydrochloride (or 1-adamantylamine) is preferably in a range from 2:1 to 10:1, more preferably from 2.01:1 to 5:1, more particularly 2.1:1 to 3:1.

The simplest way of isolating the product is to separate the organic phase from the aqueous phase. A further option is the addition of an organic solvent, for example an aromatic hydrocarbon, such as benzene, toluene or xylene. By adding an organic solvent it is possible as and when required to improve phase separation. The organic product phase can if desired by subjected to a workup by customary methods. Such methods include, for example, washing with aqueous media or separation from added solvent, by evaporation, for example.

In accordance with the second version the 1-adamantyldimethylamine is obtained in the form of an ammonium salt. The conversion into 1-adamantyldimethylamine may be accomplished with an aqueous base. Examples of suitable bases include alkali metal hydroxides, such as NaOH or KOH.

In a third version of the process of the invention, the 1-adamantyldimethylamine in step A) is provided by subjecting 1-adamantylamine or a 1-adamantylammonium salt to catalytic methylation with methanol.

For the catalytic methylation in accordance with the third version it is preferred to use 1-adamantylamine.

For the catalytic methylation in accordance with the third version it is preferred to use at least one organic solvent. For the reaction in accordance with the third process version, methanol is used preferably not only as a reactant but also as a solvent. Also suitable are the aforementioned water-immiscible solvents, especially aromatic hydrocarbons, such as benzene, toluene, ethylbenzene or xylene. One specific embodiment uses a solvent mixture for the reaction that comprises xylene and methanol or is composed of xylene and methanol.

The reaction temperature is preferably in a range from 20 to 300° C., more preferably from 50 to 270° C., more particularly from 150 to 250° C.

The pressure is preferably in a range from 1 to 300 bar, more preferably from 5 to 250 bar. Temperature and pressure of the reaction are sensibly selected such that there are sufficient concentrations of the reactants in the phase in which the reaction takes place (for example, not such that the 1-adamantylamine is substantially in liquid form and the methanol substantially in gaseous form).

In one specific embodiment the reaction in accordance with the third version takes place in a plurality (e.g. 2, 3, 4, 5, etc.) of reactors. A combination of two reactors is preferred. The reactors used may be alike or different. The reactors may be connected to one another in any desired way, for example in parallel or in series. One preferred embodiment uses two reactors connected in series. Where two or more reactors are used, they may have the same or different temperatures. The temperature in the nth reactor is preferably higher by at least 10° C., more preferably by at least 20° C., more particularly by at least 30° C., than the temperature in the (n−1)th (n minus first) reactor. When two or more reactors are being used, the reaction pressure in the individual reactors may be the same or different. In one specific embodiment only some of the reactors comprise catalyst. Thus, for example, a combination of two reactors may be used, of which only one comprises catalyst. In this version, the reaction mixture may first be preheated without catalyst in one reactor and then subsequently transferred to a reactor with catalyst for the purpose of reaction. Transfer of the reaction mixture can be accomplished using, for example, a gas, with which the mixture is forced from one reactor to another. Additionally the gas may also serve to set the desired reaction pressure. A suitable gas is hydrogen. In this case hydrogen does not participate in the actual reaction, but may also serve to keep the in-use catalyst in a reduced form.

Suitable catalysts for the third version are in principle hydrogenation catalysts as described above. Preference is given to using a copper-containing heterogeneous catalyst.

Suitability in principle is possessed by a multiplicity of copper-containing catalysts, which may additionally comprise at least one further element from main group I, II, III, IV or V, from transition group I, II, IV, V, VI, VII or VIII, and from the lanthanides (IUPAC: groups 1 to 15 and the lanthanides), more particularly Ca, Mg, Al, La, Ti, Zr, Cr, Mo, W, Mn, Ni, Co, Zn, and combinations thereof. A specific embodiment of catalysts with advantageous suitability for use in the third version of the process are Raney catalysts, especially Raney copper, and also copper-containing metal alloys in the form of a Raney catalyst. Preferred Raney catalysts are those whose metal component is composed to an extent of at least 95%, more particularly at least 99%, of copper. Raney copper can be prepared in conventional manner by subjecting copper-aluminum alloys to treatment with alkali metal hydroxides.

Another specific embodiment of catalysts with particularly advantageous suitability for use in the third version of the process are catalysts which comprise copper in oxidic form and also, optionally, additionally in elemental form.

Examples of suitable catalysts are those which comprise, on a silica support, nickel and copper, as well as other metals, as active constituents. Catalysts of this kind are described in DE-A 26 28 987, for example. The active mass of these catalysts comprises especially 40% to 80% by weight nickel, 10% to 50% by weight copper, and 2% to 10% by weight manganese. EP-A-0 434 062 describes hydrogenation catalysts which are obtainable by reducing a precursor of oxides of copper, of aluminum, and of at least one other metal selected from magnesium, zinc, titanium, zirconium, tin, nickel, and cobalt. Also suitable are the hydrogenation catalysts described in DE 102 18 849, which comprise 0.1% to 10% by weight chromium, calculated as $Cr_2O_3$, 0.1% to 10% by weight calcium, calculated as CaOx, and 5% to 20% by weight copper, calculated as CuO, deposited on a silicon dioxide support material, and based in each case on the total weight of the calcined catalyst. Known from DE-A-40 21 230 are copper-zirconium oxide catalysts, the ratio of copper atoms to zirconium atoms, expressed as a weight ratio, being 1:9 to 9:1. DE-A-4 028 295 describes suitable copper-manganese hydrogenation catalysts. EP-A-552 463 describes catalysts with an oxidic form corresponding substantially to the composition $Cu_aAl_bZr_cMn_dO_x$, in respect of which the following relationships apply: $a>0$; $b>0$; $c\geq 0$; $d>0$; $a>b/2$; $b>a/4$; $a>c$; $a>d$; and x identifies the number of oxygen ions needed in order to ensure electroneutrality per formula unit. EP-A-552 463 also describes catalysts with a lower fraction of aluminum oxide. The catalyst according to that embodiment corresponds substantially to the composition $Cu_aAl_bZr_cMn_dO_x$, in respect of which the following relationships apply: $a>0$; $a/40\leq b\leq a/4$; $c\geq 0$; $d>0$; $a>c$; $0.5d\leq a\leq 0.95d$, and x identifies the number of oxygen ions needed in order to ensure electroneutrality per formula unit. WO 2006/005505 describes shaped catalyst bodies which are particularly suitable for use in the process of the invention. In one preferred embodiment the oxidic catalyst material comprises (a) copper oxide with a fraction in the range of $50\%\leq x\leq 80\%$ by weight, preferably $55\%\leq x\leq 75\%$ by weight, (b) aluminum oxide with a fraction in the range of $15\%\leq y\leq 35\%$ by weight, preferably $20\%\leq y\leq 30\%$ by weight, and (c) at least one of the oxides of lanthanum, tungsten, molybdenum, titanium or zirconium, preferably of lanthanum and/or tungsten, with a fraction in the range of $2\%\leq z\leq 20\%$ by weight, preferably $3\%\leq z\leq 15\%$ by weight, based in each case on the total weight of the oxidic material after calcining, and subject to the following conditions: 80≤x+y+z≤100, particularly 95≤x+y+z≤100. Preferred catalysts for the third variant of the process comprise the following metals in oxidic form, reduced form (elemental form) or a combination thereof. Metals which are stable in more than one oxidation state may be used entirely in one of the oxidation states or in different oxidation states:

Cu
Cu, Ti
Cu, Zr
Cu, Mn
Cu, Al
Cu, Ni, Mn
Cu, Al, at least one further metal selected from La, W, Mo, Mn, Zn, Ti, Zr, Sn, Ni, and
Co
Cu, Zn, Zr
Cu, Cr, Ca
Cu, Cr, C
Cu, Al, Mn, optionally Zr.

As inert support material for the catalysts of the invention it is possible to use virtually all of the prior-art support materials as used advantageously in the preparation of supported catalysts, examples being $SiO_2$ (quartz), porcelain, magnesium oxide, tin dioxide, silicon carbide, $TiO_2$ (rutile, anatase), $Al_2O_3$ (alumina), aluminum silicate, steatite (magnesium silicate), zirconium silicate, cerium silicate or mixtures of these support materials. Preferred support materials are aluminum oxide and silicon dioxide.

The catalysts can be employed in the form of shaped bodies, in the form, for example, of spheres, rings, cylinders, cubes, cuboids or other geometrical bodies. Unsupported catalysts can be shaped by customary methods, as for example by extruding, tableting, etc. The shape of supported catalysts is determined by the shape of the support. As an alternative to this, the support, before or after the catalytically active component(s) is or are applied, can be subjected to a shaping method. The catalysts may be used, for example, in the form of pressed cylinders, tablets, pellets, wagon wheels, rings, stars or extrudates, such as solid extrudates, polylobal extrudates, hollow extrudates, and honeycombs or other geometrical bodies.

In step A) the reaction of the 1-adamantyldimethylamine with dimethyl sulfate takes place preferably at an elevated temperature, i.e., at a temperature which is above the ambient temperature (20° C.). The temperature in step A) is preferably at least 40° C., more preferably at least 80° C. Preferably the reaction in step A) takes place at a temperature in the range of above 100 to 220° C., more preferably of 120 to 200° C.

In one preferred embodiment in step A) first of all the 1-adamantyldimethylamine is contacted with the dimethyl sulfate at a temperature of not more than 30° C. and subsequently the resulting mixture is heated to a temperature of at least 40° C. for the purpose of further reaction. Contacting of the 1-adamantyldimethylamine with the dimethyl sulfate takes place preferably at a temperature of not more than 20° C., more particularly at a temperature of not more than 10° C. The contacting of the 1-adamantyldimethylamine with the dimethyl sulfate takes place preferably in portions. For this purpose the amine or dimethyl sulfate may be introduced and the other component, respectively, may be added in portions. Preferably the mixture, for the purpose of further reaction, is heated to a temperature of at least 80° C., more preferably 100 to 220° C., more particularly from 120 to 200° C.

The reaction of the 1-adamantyldimethylamine with the dimethyl sulfate in step A) takes place preferably in the presence of a solvent which is inert under the reaction conditions. Examples of suitable solvents include water, water-miscible solvents, and mixtures thereof. Preferred water-miscible solvents are alcohols, such as methanol, ethanol, n-propanol, isopropanol, n-butanol, and mixtures thereof. As solvent it is preferred to use water or a solvent mixture which comprises at least 30%, preferably at least 50%, more particularly at least 80% by volume of water. One specific embodiment uses water as solvent in step A).

The 1-adamantyldimethylamine and the dimethyl sulfate are preferably both used in liquid form. The dimethyl sulfate is preferably used in a pure form. The 1-adamantyldimethylamine is preferably used in combination with water or with a mixture of water and at least one water-miscible solvent. Preferably, the 1-adamantyldimethylamine, optionally in combination with a solvent, is introduced initially and the dimethyl sulfate is added.

The reaction in step A) takes place preferably at ambient pressure or under increased pressure. In one specific embodiment the reaction takes place under the autogenous pressure of the reaction mixture under the reaction conditions. The pressure during the reaction in step A) in general is preferably at least 1.1 bar, more preferably at least 2 bar, more particularly at least 5 bar. If desired, the pressure during the reaction in step A) can be up to 300 bar, preferably up to 100 bar. Suitable pressure-resistant reactors are known to the skilled worker and are described in, for example, Ullmann's Enzyklopädie der technischen Chemie, volume 1, 3rd edition, 1951, p. 769 ff. Generally speaking, for implementation of the process of the invention under increased pressure, a pressure vessel is used which, if desired, may be fitted with a stirring apparatus and/or an internal lining.

The molar amount ratio of 1-adamantyldimethylamine to dimethyl sulfate is preferably at least 2:1. More preferably the molar amount ratio of 1-adamantyldimethylamine to dimethyl sulfate is in a range from 2:1 to 20:1, more particularly 2.05:1 to 10:1, especially 2.1:1 to 5:1.

The reaction in step A) may take place if desired in the presence of at least one inert gas. Examples of suitable inert gases include nitrogen, helium, and argon.

The reaction in step A) may take place continuously or batchwise.

In general it is possible to use the reaction mixture obtained in step A), without isolation of the 1-adamantyltrimethylammonium sulfate beforehand, for the ion exchange in step B).

The reaction mixture obtained in step A) can be subjected to at least one workup step before the reaction in step B). One example is the partial or complete removal of solvent. A further example is the removal of unconverted 1-adamantyldimethylamine or of undesired by-products such as 1-adamantyltrimethylammonium methylsulfate. In general, it is possible in step A) to prevent the formation of 1-adamantyltrimethylammonium methylsulfate to such an extent that the resulting reaction mixture can be used for ion exchange in step B) without removal of at least a portion of this compound.

The workup of the reaction mixture obtained in step A) may take place in accordance with customary methods known to the skilled worker. A preferred workup is for the concentration of the 1-adamantyltrimethylammonium methylsulfate, by means, for example, of evaporation of volatile components.

In one embodiment of the process of the invention the reaction mixture obtained in step A) is subjected to partial or complete removal of the solvent. This is the case especially if the ion exchange in step B) is to take place in a solvent different from that of the alkylation in step A). It is also the case if the ion exchange in step B) is to take place in not too great a quantity of solvent. The solvent may be wholly or partly removed by means, for example, of evaporation, preferably under reduced pressure. Because the 1-adamantyltrimethylammonium salts obtained are not volatile, the pressure range employed is generally not critical. Where the desire is for complete or near-complete removal of the solvent, a fine vacuum of $10^1$ to $10^{-1}$ Pa or a high vacuum of $10^{-1}$ to $10^{-5}$ Pa may be employed, for example. To generate such reduced pressures it is possible to employ customary vacuum pumps, such as liquid jet vacuum pumps, rotary vane and rotary piston vacuum pumps, diaphragm vacuum pumps, diffusion pumps, etc. The removal of the solvent may take place, if desired, at an elevated temperature. Solvent removal is accomplished preferably at a temperature of up to 150° C., more preferably up to 100° C.

In one specific embodiment the reaction in step A) takes place in water as solvent, and the reaction mixture obtained in step A) is subjected to distillative workup to remove some of the water and, if present, unreacted 1-adamantyldimethylamine. In accordance with this embodiment, an aqueous solution of 1-adamantyltrimethylammonium sulfate is obtained in step A).

Step A) preferably produces a methylation product which comprises at least 95%, more preferably at least 99%, more particularly at least 99.9%, by weight, of 1-adamantyltrimethylammonium sulfate, based on the total weight of 1-adamantyltrimethylammonium sulfate and 1-adamantyltrimethylammonium methylsulfate.

Step B)

In accordance with the invention the 1-adamantyltrimethylammonium sulfate obtained in step A) is subjected to an ion exchange. In the course of this operation the sulfate ions and, if the starting material used for the exchange additionally comprises methylsulfate ions, then the methylsulfate ions as well are exchanged for hydroxide ions.

Ion exchangers suitable for the ion exchange are in principle the basic ion exchangers known to the skilled worker that have at least one base immobilized on a solid phase. The solid phase of these basic ion exchangers comprises, for example, a polymer matrix. These include, for example, polystyrene matrices which in addition to styrene comprise in copolymerized form at least one crosslinking monomer, divinylbenzene for example, and also, optionally, further comonomers. Also suitable are polyacrylic matrices which are obtained by polymerizing at least one (meth)acrylate, at least one crosslinking monomer, and, optionally, further comonomers. Other suitable polymer matrices are phenol-formaldehyde resins and polyalkylamine resins, which are obtained, for example, by condensing polyamines with epichlorohydrin.

The anchor groups which are bound directly or via a spacer group to the solid phase (and whose loosely bound counterions can be replaced by ions bearing a charge of the same sign) are preferably selected from nitrogen-containing groups, preferably tertiary and quaternary amino groups.

Suitable functional groups are, for example:
—$CH_2N^+(CH_3)_3$ $OH^-$ e.g., Duolite A 101, Ambersep 900 OH
—$CH_2N^+(CH_3)_2CH_2CH_2OHOH^-$ e.g., Duolite A 102, Amberlite IRA 410
—$CH_2N^+(C_3H_7)_3OH^-$ e.g., Ionac SR 7

Both strongly and weakly basic ion exchangers are suitable for the process of the invention. Strongly basic ion exchangers are preferred. Strongly basic (an)ion exchangers are anion exchangers which in the unloaded form possess strongly basic functional groups, as example quaternary ammonium groups with hydroxide ions as counterions. In contrast to weakly basic anion exchangers, they can generally be used without prior protonation even in neutral or basic solution. Strongly basic anion exchangers can be regenerated by treatment with aqueous solutions of strong bases, such as NaOH or KOH. Weakly basic anion exchangers are anion exchangers which possess weakly basic functional groups. These include, for example, primary, secondary or tertiary amino groups. They can be regenerated by the aforementioned strong bases, but also by weak bases, such as alkali metal carbonates or ammonia solution. Preferred among the weakly basic ion exchangers are those which have tertiary amino groups.

Preference for use in the process of the invention is given to strongly basic ion exchangers.

Commercially available ion exchangers suitable for the process of the invention are, for example, Amberlyst® A27 (quaternary ammonium groups, strongly basic) and Ambersep® 900 OH (strongly basic). Other suitable anion exchangers are, for example, the Amberlite, Duolite and Purolite resins from Rohm & Haas, such as Amberlite IRA-402, IRA-458, IRA-900. Also suitable are IMAC HP 555, Amberjet 4200 and Amberjet 4400. Further suitable anion exchangers are, for example, the Lewatit resins from BAYER AG, such as Lewatit M 500, MP500 etc. Other suitable anion exchangers are, for example, the Dowex products from Dow, such as DOWEX SBR-P, SAR, MARATHON MSA, 22, etc.

For the ion exchange, the ion exchangers, if necessary, are first loaded with OH ions and then brought into contact with a solution comprising the 1-adamantyltrimethylammonium sulfate obtained in step A). As solvent it is preferred to use water.

For the ion exchange in step B), it is preferred to employ an aqueous solution which comprises 1-adamantyltrimethylammonium sulfate in a concentration of 2% to 20% by weight, more preferably 5% to 15% by weight.

The treatment with the anion exchanger takes place in a customary way, as for example by contacting the aqueous solution comprising 1-adamantyltrimethylammonium sulfate with the ion exchanger in a vessel or, preferably, passing said solution over a bed of the ion exchanger, especially a column packed with the ion exchanger.

The ion exchange in step B) may be carried out continuously or batchwise. Continuous operation is preferred. For that purpose a combination of a plurality of (e.g., 2, 3, 4, 5, etc.) ion exchanger columns can be used, with some of the columns being used for ion exchange at the same time as others are subjected to regeneration.

In one specific embodiment of the process of the invention, step B) produces an aqueous 1-adamantyltrimethylammonium hydroxide solution which can be concentrated by being subjected to partial separation from water.

Generally speaking, the aqueous 1-adamantyltrimethylammonium hydroxide solution obtained following anion exchange on the ion exchanger loaded with OH ions has a 1-adamantyltrimethylammonium hydroxide content of at least 1%, preferably of at least 3%, more particularly at least 5%, by weight, based on the total weight of the solution.

The partial separation from water may take place in accordance with customary methods known to the skilled worker. Suitability for such methods is possessed by customary evaporators, which at their most simple comprise a container having heatable heat-exchange surfaces. Preference is given to using a thin-film evaporator, such as a falling-film evaporator, for example. Also suitable are evaporators with moving internals, in which, for example, wiper blades produce a thin film of liquid on the inner wall of the evaporator. These include thin-film evaporators of the "LUWA"® or "SAM- BAY"® type. Evaporation takes place preferably at a temperature in the range from 0 to 150° C., more preferably 10 to 120° C., more particularly 20 to 100° C. Evaporation takes place preferably at a pressure in the range from 0.01 mbar to 1013 mbar, more preferably from 0.1 mbar to 500 mbar, more particularly 1 to 250 mbar.

The 1-adamantyltrimethylammonium hydroxide solution obtained by the process of the invention (optionally after partial separation from water) preferably has a 1-adamantyltrimethylammonium hydroxide content of at least 10%, more preferably at least 15%, more particularly at least 18%, by weight, based on the total weight of the solution.

EXAMPLES

Example 1

Liberation of 1-Adamantylamine from 1-Adamantylammonium Hydrochloride with Aqueous Sodium Hydroxide Solution A 10 m$^3$ stirred tank (filled to 80% of its capacity) equipped for operation under inert gas is charged with 1380 kg of 1-adamantylammonium hydrochloride under a nitrogen atmosphere, and 5170 l of xylene are added. At atmospheric pressure, 1840 l of 20% strength aqueous sodium hydroxide solution are metered in over the course of 30 minutes, with stirring, and the reaction mixture is subsequently stirred for two hours, in the course of which the hydrochloride dissolves and 1-adamantylamine is liberated. Following phase separation, the aqueous phase is drained off and the organic phase is stirred with 300 l of 1% strength aqueous sodium hydroxide solution. The aqueous phase is drained off again and the water is removed from the organic phase by stirred extraction with 300 l of 50% strength aqueous sodium hydroxide solution. Subsequently the aqueous phase is drained off again. This results in 4384 l of an approximately 32% xylenic solution of 1-adamantylamine, with a residual water content of about 0.13%. The combined aqueous phases are stirred once with 1720 l of xylene in order to remove dissolved 1-adamantylamine. The resultant organic phase is used as a solvent in the liberation of the next batch of 1-adamantylamine.

The yield of liberated adamantylamine is 99.8%.

Example 2

Preparation of 1-Adamantyldimethylamine by Reductive Amination of Formaldehyde with 1-Adamantylamine and Hydrogen in the Presence of Raney Nickel A 10 m$^3$ stirred tank (filled to 80% of its capacity) equipped for operation under inert gas is charged under nitrogen with 5501 kg of 25% strength xylenic 1-adamantylamine solution from example 1. With stirring, 138 kg of Raney nickel catalyst and 55 kg of a 30% strength aqueous NaH$_2$PO$_4$ solution are added. The reactor is gassed with hydrogen until an internal pressure of 5 bar is reached, after which it is heated to 100° C. An internal reactor pressure of 50 bar is set by further addition of hydrogen. Subsequently, with stirring, over the course of three hours, 1905 kg of a 30% strength formaldehyde solution are metered in, followed by stirring for two hours more at 100° C. After the reaction mixture has been cooled and the reactor has been let down, the liquid contents of the reactor are emptied and the discharge is filtered to give a two-phase filtrate. This filtrate is admixed with 73 kg of 25% strength aqueous sodium hydroxide solution in a tank, with stirring.

After 15 minutes of stirring, the phases are separated and the organic phase is subjected to distillation for separation of the xylene. The 1-adamantyldimethylamine is obtained as the bottom product in this procedure. Yield: >99%

Example 3

Preparation of 1-Adamantyldimethylamine by Reductive Amination of Formaldehyde with 1-Adamantylamine in the Presence of Formic Acid (Eschweiler-Clark)

A 2.5 m$^3$ stirred reactor equipped for operation under inert gas is charged under nitrogen with 570 kg of 1-adamantylammonium hydrochloride, and 901 kg of a 30% strength formaldehyde solution are added at room temperature and with stirring. Subsequently the reaction mixture is heated to 60° C. and stirred for an hour in order for the hydrochloride to dissolve. Thereafter 422 kg of formic acid are added at 60° C. The reactor is heated slowly to 90° C. and stirred at that temperature for 115 to 125 h, the reaction being monitored by gas chromatography. When reaction has been brought to an end, the reactor is cooled to 45° C. and 732 kg of 50% strength aqueous sodium hydroxide solution are added at a metering rate of approximately 100 kg/hour, the internal temperature not exceeding 50° C. Thereafter the reactor is cooled to 25° C. and the phases are separated. The organic phase is isolated and residual water is separated off by distillation at 70 mbar with a bottom temperature of 80° C. In the course of the distillation the pressure is reduced further to 5 mbar and subsequently the bottom product is heated to 100° C. After the end of distillation, the 1-adamantyldimethylamine is obtained as the top product. Yield 97% to 98%, purity by gas chromatography: 99.5 to 99.6 area %.

Example 4

Preparation of 1-Adamantyldimethylamine by Catalytic Methylation of 1-Adamantylamine with Methanol 4.1 Batch Procedure:

The reaction takes place in two 270 ml autoclaves connected to one another by thin pipelines. The second autoclave is charged with 10 g of a CuO catalyst on Al$_2$O$_3$, and the catalyst is activated for two hours at 200° C. under 200 bar of hydrogen (the catalyst is reused 3× without loss of activity). Introduced into the first autoclave is a solution of 15% 1-adamantylamine, 35% xylene and 50% methanol, and then the first autoclave is heated to 90° C. and the second autoclave to 220° C. After 10 minutes the reaction mixture is transferred from the first to the second autoclave using hydrogen. In the second autoclave the reaction is carried out with stirring at 200° C. and 100 bar for four hours. A quantitative conversion of 1-adamantylamine to 1-adamantyldimethylamine is achieved. Yield: >99%

For the isolation of the 1-adamantyldimethylamine the reaction product is subjected to distillative removal of the methanol, the xylene, and the water liberated during the reaction.

4.2 Continuous Procedure (Laboratory Equipment):

A tube reactor (18×3×770 mm) is charged with 51.4 g of CuO catalyst on Al$_2$O$_3$ (tablets) (catalyst bed height: about 500 mm). The tube reactor is traversed continuously by a flow of a mixture of the ingredients (liquid-phase mode, 94.0 g/h); the composition of the feed is 15% adamantylamine, 35% xylene, and 50% methanol. With a space velocity of 0.25 kg of adamantylamine/l*h, >99% of 1-adamantyldimethylamine is obtained at 80 bar and 230° C.

4.3 Continuous Procedure (Pilot Plant):

A tube reactor (4.85 l) is charged with 4394.0 g of CuO catalyst on $Al_2O_3$ (tablets). The tube reactor is traversed continuously by a flow of a mixture of the ingredients (liquid-phase mode, 9365.0 g/h); the composition of the feed is 13% adamantylamine, 37% xylene, and 50% methanol. With a space velocity of 0.25 kg of adamantylamine/l*h, >99% of 1-adamantyldimethylamine is obtained at 80 bar and 195° C.

Example 5

Quaternization of 1-Adamantyldimethylamine with Dimethyl Sulfate

A 2.5 m³ stirred vessel is charged with 2.5 t of water and 533 kg of 1-adamantyldimethylamine. Subsequently, 191 kg of dimethyl sulfate are metered in and the resulting reaction mixture is reacted at 30 to 50° C. for 2 hours. Subsequently the tank is heated to 140° C., an internal pressure of 4 bar being attained, and reaction continues at this temperature for 16 hours. The quaternization product is subjected to distillative removal of water, giving a 30% to 33% strength by weight solution of 1-adamantyltrimethylammonium sulfate. Conversion: 99%

Example 6

Preparation of 1-Adamantyltrimethylammonium Sulfate by Ion Exchange

1-Adamantyltrimethylammonium sulfate is used as a 30% strength solution and in a static mixer is mixed with recycled wash water to give a 10% strength solution. This solution is run at ambient temperature from below into an ion exchanger column. The amount is approximately 1.3 bed volumes. In this system, the sulfate ions and (where present) methylsulfate ions are replaced by hydroxide ions. Thereafter the column is rinsed free of product with fully demineralized water and recycled wash water (a total of approximately 3 bed volumes). One portion of the discharge from the ion exchanger is isolated as the product of value; the other portion is collected as wash water and is employed as wash water or dilution water in the subsequent cycle. Subsequently the ion exchanger column is regenerated with 7% strength by weight aqueous sodium hydroxide solution (3 bed volumes) and washed free of alkali with 4.5 bed volumes of fully demineralized water and recycled wash water. The product of value is concentrated to 20% by distillative removal of water under an absolute pressure of 130 mbar and at a temperature of approximately 50° C.

The invention claimed is:

1. A process for preparing 1-adamantyltrimethylammonium hydroxide, comprising:
   A) reacting 1-adamantyldimethylamine with dimethyl sulfate to give 1-adamantyltrimethylammonium sulfate; and
   B) subjecting the 1-adamantyltrimethylammonium sulfate obtained in A) to anion exchange with an ion exchanger loaded with OH ions.

2. The process of claim 1, wherein the 1-adamantyldimethylamine is obtained by subjecting 1-adamantylamine or a 1-adamantylammonium salt to a dimethylation.

3. The process of claim 2, wherein the 1-adamantyldimethylamine is obtained from 1-adamantylammonium hydrochloride.

4. The process of claim 3, wherein the 1-adamantylammonium hydrochloride is reacted with aqueous base to form 1-adamantylamine.

5. The process of claim 1, wherein the 1-adamantyldimethylamine is obtained by subjecting formaldehyde to a reductive amination with 1-adamantylamine or a 1-adamantylammonium salt and hydrogen in the presence of a hydrogenation catalyst.

6. The process of claim 5, wherein the reductive amination occurs in a system having two liquid phases.

7. The process of claim 5, wherein the reductive amination is carried out with a solvent mixture comprising water and at least one aromatic hydrocarbon.

8. The process of claim 5, wherein the hydrogenation catalyst comprises Raney nickel.

9. The process of claim 5, wherein a reductive amination product is distilled.

10. The process of claim 5, wherein 1-adamantylamine is obtained by treating 1-adamantylammonium hydrochloride with an aqueous solution of a base.

11. The process of claim 1, wherein the 1-adamantyldimethylamine is obtained by subjecting formaldehyde to a reductive amination with 1-adamantylamine or a 1-adamantylammonium salt in the presence of formic acid.

12. The process of claim 1, wherein the 1-adamantyldimethylamine is obtained by subjecting 1-adamantylamine or a 1-adamantylammonium salt to catalytic methylation with methanol.

13. The process of claim 1, wherein the reacting A) with dimethyl sulfate occurs at a temperature of at least 40° C.

14. The process of claim 1, wherein a molar amount ratio of 1-adamantyldimethylamine to dimethyl sulfate is at least 2:1.

15. The process of claim 1, wherein the reacting A) produces a methylation product comprising at least 95%, by weight, of 1-adamantyltrimethylammonium sulfate, based on the total weight of 1-adamantyltrimethylammonium sulfate and 1-adamantyltrimethylammonium methylsulfate.

16. The process of claim 1, where the ion exchanger is a strongly basic anion exchanger.

17. The process of claim 1, further comprising:
   C) optionally subjecting an aqueous 1-adamantyltrimethylammonium hydroxide solution obtained from the anion exchange B) to a partial separation from water.

18. The process of claim 17, wherein the aqueous 1-adamantyltrimethylammonium hydroxide solution is subjected to the partial separation from water, and the resulting solution has a 1-adamantyltrimethylammonium hydroxide content of at least 10%, by weight, based on the total weight of the solution.

19. The process of claim 5, wherein the reductive amination is carried out with a solvent mixture comprising water and xylene.

20. The process of claim 1, wherein the reacting A) with dimethyl sulfate occurs at a temperature of at least 80° C.

* * * * *